US012788370B2

(12) United States Patent
Kim et al.

(10) Patent No.: US 12,788,370 B2
(45) Date of Patent: Nov. 10, 2026

(54) INFORMATION PROVIDING DEVICE METHOD FOR GENERATING PULSE-COMPRESSED ULTRAFAST DOPPLER IMAGE

(71) Applicants: Daegu Gyeongbuk Institute of Science and Technology, Dalseong-gun (KR); POSTECH Research and Business Development Foundation, Pohang-si (KR)

(72) Inventors: Chul Hong Kim, Pohang-si (KR); Jaesok Yu, Daegu (KR); Dong Hyeon Oh, Pohang-si (KR); Nizar Guezzi, Daegu (KR)

(73) Assignees: Daegu Gyeongbuk Institute of Science and Technology, Daegu (KR); POSTECH Research and Business Development Foundation, Pohang-si (KR)

( * ) Notice: Subject to any disclaimer, the term of this patent is extended or adjusted under 35 U.S.C. 154(b) by 0 days.

(21) Appl. No.: 19/044,785

(22) Filed: Feb. 4, 2025

(65) Prior Publication Data

US 2026/0102144 A1 Apr. 16, 2026

(30) Foreign Application Priority Data

Oct. 16, 2024 (KR) ........................ 10-2024-0141626

(51) Int. Cl.
*A61B 8/00* (2006.01)
*A61B 8/06* (2006.01)
(Continued)

(52) U.S. Cl.
CPC ................ *A61B 8/488* (2013.01); *A61B 8/06* (2013.01); *A61B 8/0891* (2013.01);
(Continued)

(58) Field of Classification Search
CPC ......... A61B 8/488; A61B 8/06; A61B 8/0891; A61B 8/5215; G06T 7/20; G06V 10/25; G16H 30/20; G16H 30/40
See application file for complete search history.

(56) References Cited

U.S. PATENT DOCUMENTS

2012/0063665 A1* 3/2012 Wang .................. A61B 5/7203 382/130
2018/0275272 A1 9/2018 Questa
(Continued)

FOREIGN PATENT DOCUMENTS

CN 103784166 A * 5/2014
CN 110831487 A * 2/2020 ........... A61B 1/0005
(Continued)

OTHER PUBLICATIONS

Communication dated Jun. 16, 2026, issued in Korean Application No. 10-2024-0141626.
(Continued)

*Primary Examiner* — Kaitlyn E Sebastian
(74) *Attorney, Agent, or Firm* — Sughrue Mion, PLLC

(57) ABSTRACT

The information providing device according to an embodiment of the present invention may include a processor configured to receive a reflected signal that reflected by transmitting an ultrafast ultrasound signal designed according to a transmission mode to a target region, compress a pulse of the reflected signal using a decoding filter according to the transmission mode, obtain an image reconstructing the compressed signal through a dynamic beamforming, remove a fixed tissue signal from the image using a clutter filter, and generate a pulse-compressed ultrafast Doppler image by inversely compensating for an estimated displacement according to motion tracking for a region of interest in the image including a dynamic blood flow signal.

15 Claims, 12 Drawing Sheets

(51) Int. Cl.

| | |
|---|---|
| ***A61B 8/08*** | (2006.01) |
| ***G06T 7/20*** | (2017.01) |
| ***G06V 10/25*** | (2022.01) |
| ***G16H 30/20*** | (2018.01) |
| ***G16H 30/40*** | (2018.01) |

(52) U.S. Cl.

CPC .............. *A61B 8/5215* (2013.01); *G06T 7/20* (2013.01); *G06V 10/25* (2022.01); *G16H 30/20* (2018.01); *G16H 30/40* (2018.01)

(56) References Cited

U.S. PATENT DOCUMENTS

| | | | | |
|---|---|---|---|---|
| 2019/0353764 | A1* | 11/2019 | Vignon | A61B 8/14 |
| 2022/0211350 | A1* | 7/2022 | Pinton | G01S 15/899 |
| 2023/0277156 | A1* | 9/2023 | Collins | G06N 3/096 382/128 |

FOREIGN PATENT DOCUMENTS

| | | | | | |
|---|---|---|---|---|---|
| CN | 109342543 | B | * | 7/2021 | G01N 27/622 |
| JP | 11-309145 | A | | 11/1999 | |
| JP | 11-309146 | A | | 11/1999 | |
| JP | 11-309147 | A | | 11/1999 | |
| JP | 2007-020915 | A | | 2/2007 | |
| JP | 2022-172303 | A | | 11/2022 | |
| JP | 2024-510579 | A | | 3/2024 | |
| WO | WO-2024171356 | A1 | * | 8/2024 | G06T 7/70 |

OTHER PUBLICATIONS

Vienneau et al., "A Coded Excitation Framework for Increased Signal-to-Noise Ratio of in Vivo Ultrasound Power Doppler Imaging", Proc of SPIE, 2021, vol. 11602, 7 pages.

Osmanski et al., "Ultrafast Doppler Imaging of Blood Flow Dynamics in the Myocardium", IEEE Transactions On Medical Imaging, Aug. 2012, vol. 31, No. 8, pp. 1661-1668.

* cited by examiner

INFORMATION PROVIDING DEVICE METHOD FOR GENERATING PULSE-COMPRESSED ULTRAFAST DOPPLER IMAGE

CROSS-REFERENCE TO RELATED APPLICATION

This application claims priority to and the benefit of Korean Patent Application No. 10-2024-0141626, filed on Oct. 16, 2024, the disclosures of which is incorporated herein by reference in its entirety.

TECHNICAL FIELD

The present disclosure relates to an information providing device and method for generating a pulse-compressed ultrafast Doppler image.

RELATED ART

Diabetes affects about 537 million adults in 2021, and 240 million undiagnosed people face a fatal risk because untreated diabetes may lead to serious complications. Chronic kidney disease (CKD), especially diabetic nephropathy, accounts for 27.8% of diabetic complications and is the leading cause of death in diabetic patients, causing unnecessary kidney damage requiring lifelong dialysis or kidney transplantation. Therefore, it is most important to preserve the kidney function before deterioration. To evaluate the kidney function, the current clinical practice measures or estimates the degree of removing wastes from blood or urine samples called glomerular filtration rate (GFR). Since the glomerular filtration rate is a delay indicator of kidney damage, it is not easy to prevent or intervene early until signs are detected. In addition, the anemia symptoms of patients who lose 20-50% of kidney function due to chronic kidney disease become more severe as kidney function deteriorates, and most of the serious patients face the burden of blood collection.

Meanwhile, kidney filtration is mainly driven by microcirculation within the glomerular, and the non-invasive image of the kidney microcirculation may serve as a leading indicator to detect kidney damage and prevent significant loss of function.

Conventional clinical angiography methods have limitations in visualizing microcirculation of kidney. Both X-ray computed tomography angiography (CTA) and magnetic resonance angiography (MRA) are not suitable for identifying delicate interlobular blood vessels due to limited spatiotemporal resolution and are not sensitive to microvascular hemodynamics. In addition, CTA and MRA contrast agents are contraindicated in patients with chronic kidney disease whose kidney is damaged because contrast agent residues may contribute to contrast agent-induced nephropathy or nephrogenic systemic fibrosis.

Doppler ultrasound image may visualize the kidney hemodynamics that change with time even without the use of contrast agents. However, conventional Doppler ultrasound image captures major blood flow, but lacks the ability to contrast slow microvascular flow due to the lack of continuous samples used for blood flow estimation.

Ultrafast Doppler imaging (UFD) overcomes these barriers and dramatically increases the number of samples at ultrafast scales (for example, 6,667 Hz pulse repetition frequency (PRF) at 100 mm depth) through accelerated frame collection, allowing microvascular contrast at scales of less than 1 mm. Taking advantage of these advantages, ultrafast Doppler image has been found to be used to investigate a wide range of pathological blood vessel changes, including brain, myocardium, and liver.

Nevertheless, the conventional ultrafast Doppler image is promising to visualize human microvascular, but it is still difficult to image organs located deep in the body such as kidney. In general, the ultrafast Doppler image technology transmits plane waves to accelerate frame acquisition, but the echo signal is weak due to out-of-focus and low acoustic pressure. In addition, when a high-frequency ultrasound transducer is implemented to increase the spatial resolution, severe tissue attenuation occurs, so the penetration depth is limited.

Therefore, the conventional ultrafast Doppler imaging technology must compromise on low spatial resolution by using a low-frequency ultrasound transducer or involving invasive procedures such as surgical incision or ultrasound contrast injection due to the relatively shallow penetration depth. As a result, transmission acoustic power may be increased, but there is a limit in terms of sound radiation safety to prevent tissue damage. Therefore, there is an urgent need to develop a new ultrafast Doppler imaging method that non-invasively images the entire human kidneys with the highest resolution and signal-to-noise ratios (SNRs).

SUMMARY

An object of the present disclosure is to provide an information providing device and method for generating a more improved ultrafast Doppler image.

An object of the present disclosure is to provide an information providing device and method for evaluating an ultrafast Doppler image that may replace the diagnosis of conventional chronic kidney disease that depends on the glomerular filtration rate.

The objects of the present disclosure are not limited to the aforementioned objects, and other objects that are not mentioned can be clearly understood by those skilled in the art from the following description.

The information providing device according to an embodiment of the present invention may include a processor configured to receive a reflected signal that reflected by transmitting an ultrafast ultrasound signal designed according to a transmission mode to a target region, compress a pulse of the reflected signal using a decoding filter according to the transmission mode to produce a compressed signal, obtain an image reconstructing the compressed signal through a dynamic beamforming, remove a fixed tissue signal from the image using a clutter filter, and inversely compensate for an estimated displacement according to motion tracking for a region of interest in the image including a dynamic blood flow signal to generate a pulse-compressed ultrafast Doppler image.

The processor may evaluate the pulse-compressed ultrafast Doppler image using a hemodynamic parameter related to a blood vessel area and a perfusion and a blood vessel skeletal parameter related to a blood vessel density and a blood vessel tortuosity.

The processor may identify the hemodynamic parameter related to the blood vessel area based on a ratio of the blood vessel area to an area of the target region.

The processor may identify the hemodynamic parameter related to the perfusion based on an area of the target region and a mean relative Doppler intensity of the dynamic blood flow signal.

The processor may identify the blood vessel skeletal parameter related to the blood vessel density based on an area of the target region and the number of blood vessel branches.

The processor may identify the blood vessel skeletal parameter related to the blood vessel tortuosity based on a linear distance of both ends of the blood vessel and a length of each of blood vessel branches.

The transmission mode may be a Barker mode or a Golay mode.

The processor may compress the pulse of the reflected signal using the decoding filter designed to remove a side lobe of the reflected signal in the Barker mode.

The processor may compress the pulse of the reflected signal using the decoding filter designed as an inverse phase of the ultrafast ultrasound signal in the Golay mode.

The processor may include a sequence configured to define detailed parameters necessary for generating the pulse-compressed ultrafast Doppler image and configure an event sequence operating in stages; and a kernel in which kernel functions defined to process the event sequence generated in the sequence are configured in parallel.

The information providing method performed by the information providing device according to an embodiment of the present disclosure may include receiving a reflected signal that reflected by transmitting an ultrafast ultrasound signal designed according to a transmission mode to a target region; compressing a pulse of the reflected signal using a decoding filter according to the transmission mode to produce a compressed signal; obtaining the image reconstructing a signal compacted through a dynamic beamforming; removing a fixed tissue signal from the image using a clutter filter; and inversely compensating for an estimated displacement according to motion tracking for a region of interest in the image including a dynamic blood flow signal to generate a pulse-compressed ultrafast Doppler image.

The information providing method may further include evaluating the pulse-compressed ultrafast Doppler image using a hemodynamic parameter related to a blood vessel area and a perfusion and a blood vessel skeletal parameter related to a blood vessel density and a blood vessel tortuosity.

The evaluating the pulse-compressed ultrafast Doppler image may include identifying the hemodynamic parameter related to the blood vessel area based on a ratio of the blood vessel area to an area of the target region.

The evaluating the pulse-compressed ultrafast Doppler image may include identifying the hemodynamic parameter related to the perfusion based on an area of the target region and a mean relative Doppler intensity of the dynamic blood flow signal.

The evaluating the pulse-compressed ultrafast Doppler image may include identifying the blood vessel skeletal parameter related to the blood vessel density based on an area of the target region and the number of blood vessel branches.

The evaluating the pulse-compressed ultrafast Doppler image may include identifying the blood vessel skeletal parameter related to the blood vessel tortuosity based on a linear distance of both ends of the blood vessel and a length of each of blood vessel branches.

The compressing a pulse of the reflected signal may include compressing the pulse of the reflected signal using the decoding filter designed to remove a side lobe of the reflected signal in the Barker mode.

The compressing a pulse of the reflected signal may include compressing the pulse of the reflected signal using the decoding filter designed as an inverse phase of the ultrafast ultrasound signal in the Golay mode.

The device for providing information according to an embodiment of the present disclosure may effectively improve a penetration depth and a signal-to-noise ratio of the ultrafast Doppler image, and may overcome tissue attenuation, and may image complex micro-blood vessels of the deep organs with high contrast and high resolution.

According to an embodiment of the present disclosure, it is possible to demonstrate the pulse-compressed ultrafast Doppler image (PC-UFD) that effectively expands the image depth for the deep organ image and improves the sensitivity of microvascular flow.

According to an embodiment of the present disclosure, the pulse compression technique may restore long encoded pulses into short pulses and deliver high energy pulses, and as a result, the image depth and the sensitivity of microvascular are greatly improved beyond hardware limitations.

According to an embodiment of the present disclosure, monitoring decreased blood flow using pulse-compressed ultrafast Doppler image may predict renal function impairment due to various complications, and is expected to be widely applied to deep organs in addition to the kidney.

It should be understood that the effects of the present disclosure are not limited to the above-described effects, but include all effects that can be inferred from the detailed description of the present disclosure or the configuration of the invention described in the claims.

DETAILED DESCRIPTION OF THE EMBODIMENTS

Figure 1:
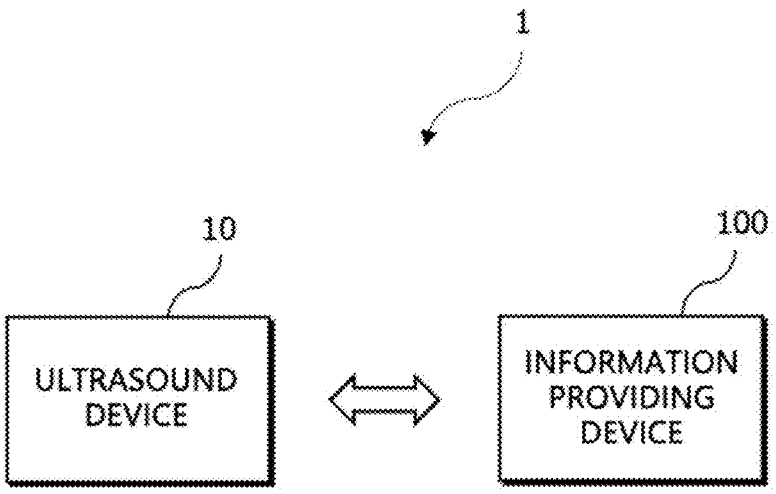
FIG. 1 is a schematic diagram showing an information providing system according to an embodiment of the present disclosure.

Hereinafter, preferred embodiments according to the present disclosure will be described in detail with reference to the accompanying drawings. The detailed description that will be set forth below in conjunction with the accompanying drawings is intended to describe exemplary embodiments of the invention and is not intended to represent the only embodiments in which the invention may be practiced. In the drawings, parts irrelevant to the description may be omitted to clearly describe the present disclosure, and the same reference numerals may be used for the same or similar components throughout the specification.

The words and terms used in the specification and claims should not be interpreted as limited to ordinary or dictionary meanings, but should be interpreted as meanings and concepts consistent with the technical idea of the present disclosure according to the principle that the inventor can define the terms and concepts in order to explain their invention in the best way.

Therefore, the embodiments and structures illustrated in the drawings described in this specification correspond to preferred embodiments of the present disclosure, and are not all representative of the technical idea of the present disclosure, so the corresponding structures may have various equivalents and modifications to replace them at the time of filing the present disclosure.

In this specification, it should be understood that the terms such as “include” or “have” are intended to explain the presence of features, numbers, steps, operations, components, parts or combinations described in the specification, and do not exclude the presence or addition possibility of one or more other features, numbers, steps, operations, components, parts or combinations thereof in advance.

FIG. 1 is a schematic diagram showing an information providing system according to an embodiment of the present disclosure.

The information providing system according to an embodiment of the present disclosure is a system 1 that generates pulse-compressed ultrafast Doppler imaging (PC-UFD) (hereinafter, referred to as a system 1). In this case, the information providing system 1 according to an embodiment of the present disclosure may include an ultrasound device 10 and an information providing device 100.

According to an embodiment of the present disclosure, the ultrasound device 10 is a device that transmits an ultrasound signal to a target region through a transducer and then receives a reflected signal that is returned. The ultrasound device 10 may operate in a plurality of modes, for example, in a brightness mode B which is a basic mode, in a Doppler mode using a Doppler effect, and the like.

In this case, the Doppler mode includes a color Doppler mode in which a direction of blood flow may be represented by color and a speed of blood flow may be represented by brightness, and a power Doppler mode in which the blood flow may be represented more sensitively than the color Doppler mode.

As such an ultrasound device, various known ultrasound devices may be used, and detailed descriptions thereof will be omitted.

According to an embodiment of the present disclosure, the information providing device 100 is connected to the ultrasound device 10 by wired/wireless communication to receive a reflected signal, and generates an ultrasound image by imaging in real time to provide the ultrasound image to a user.

According to an embodiment of the present disclosure, the information providing device 100 is a device for generating a pulse-compressed high-speed Doppler image, and may be implemented as a computer, a server, a smartphone, a tablet PC, a smart pad, a laptop, or the like. In this case, in an embodiment of the present disclosure, the information provided by the information providing device may be pulse-compressed ultrafast Doppler image information, but is not limited thereto.

In an embodiment of the present disclosure, the ultrasound device 10 and the information providing device 100 may be implemented as separate devices, or may be implemented as single device, and the implementation form is not limited to either.

As described above, ultrafast Doppler image technology has been introduced for measuring micro-blood flow, but there are still limitations in the method of imaging micro-blood flow in deep organs.

The information providing device according to an embodiment of the present disclosure may effectively improve a penetration depth and a signal-to-noise ratio beyond a resolution of the ultrafast Doppler image and a limit of hardware using the pulse compression technique, and may overcome tissue attenuation, and may image complex micro-blood vessels of the deep organs with high contrast and high resolution.

Hereinafter, the configuration and operation of the information providing device according to an embodiment of the present disclosure will be described in detail with reference to the drawings.

Figure 2:
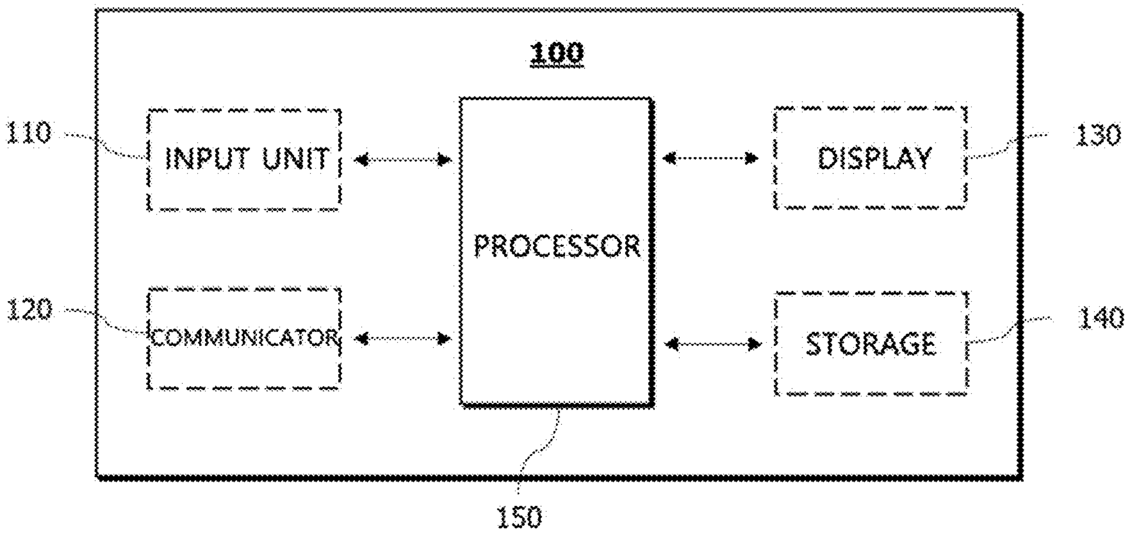
FIG. 2 is a block diagram showing a configuration of an information providing device according to an embodiment of the present disclosure.

FIG. 2 is a block diagram showing a configuration of an information providing device according to an embodiment of the present disclosure.

The information providing device 100 according to an embodiment of the present disclosure includes an input unit 110, a communicator 120, a display 130, a storage 140, and a processor 150.

The input unit 110 generates input data in response to a user input of the information providing device 100. For example, the user input may be a user input that initiates the operation of the information providing device 100, and in addition may be applied without limitation to the case of a user input necessary to generate the pulse-compressed ultrafast Doppler image and evaluate the generated image.

The input unit 110 includes at least one input means. The input unit 110 includes at least one input means. The input unit 110 may include a key board, a key pad, a dome switch, a touch panel, a touch key, a mouse, a menu button, and the like.

The communicator 120 communicates with an external device such as the ultrasound device 10, a server, and the like to transmit and receive ultrafast ultrasound signals, reflection signals, clutter filters, tissue signals, blood flow signals, and pulse-compressed ultrafast Doppler images.

Specifically, the communicator 120 may perform PCIe (PCI express) communication (6.6 GB/s) for high-bandwidth/high-capacity channel data transmission and reception, and representative interface specifications are, for example, 0.98 GB/s* (up to 16 lanes) per lane for the 3rd generation standard, 1.97 GB/s* (up to 16 lanes) per lane for the 4th generation standard, and 3.94 GB/s* (up to 16 lanes) per lane for the 5th generation standard. At this time, USB is 3.2—1st generation standard: 0.64 GB/s, 3.2—2nd generation standard: 1.28 GB/s, 3.2—2×2 generation standard: 2.56 GB/s per lane, 4—v1.0 standard: 2.56~5.12 GB/s.

In addition, the communicator 120 may perform communication such as 5th generation communication (5G), long term evolution-advanced (LTE-A), long term evolution (LTE), wireless fidelity (Wi-Fi), Bluetooth, and the like.

The display 130 displays display data according to the operation of the information providing device 100. The display 130 may display a screen for indicating pulse-compressed ultrafast Doppler images, a screen for indicating evaluation information for evaluating acquired images, a screen for receiving the user input, and the like.

The display 130 includes a liquid crystal display (LCD), a light emitting diode (LED) display, an organic light emitting diode (OLED) display, a micro electro mechanical systems (MEMS) display, and an electronic paper display. The display 130 may be combined to the input unit 110 and may be implemented as a touch screen.

The storage 140 stores operation programs of the information providing device 100. The storage 140 includes a non-volatile attribute storage capable of storing data (information) regardless of whether or not power is provided, and a volatile attribute memory in which data to be processed by the processor 150 is loaded and data cannot be stored unless power is supplied. The storage includes a flash memory, a hard-disc drive (HDD), a solid-state drive (SSD), a read only memory (ROM), and the like, and the memory includes a buffer, a random access memory (RAM), and the like.

The storage 140 may store ultrafast ultrasound signals, reflection signals, clutter filters, tissue signals, blood flow signals, pulse-compressed ultrafast Doppler images, etc. The storage 140 may store a necessary calculation program in the process of pulse compression, image reconstruction, tissue signal removal, motion tracking, pulse-compressed ultrafast Doppler image generation, hemodynamic parameter identification, and vascular skeletal parameter identification, etc.

The processor 150 may execute software such as a program to control at least one other component (e.g., hardware or software component) of the information providing device 100, and may perform various data processing or calculations.

Parallel computing is important in the image computation process, and the processor 150 may use a multi-core computing device such as a central processing unit (CPU) or graphics processing unit (GPU) for a server.

In addition, the processor 150 may be divided into 1) a sequence constituting a computation process, and 2) a kernel executing for a specific function like a function in the sequence.

In other words, the sequence may define detailed parameters necessary for generating the pulse-compressed ultrafast Doppler image and configure an event sequence operating in stages. Specifically, the sequence may configure the overall image processing flow according to the procedure, and utilize an object-oriented programming language, such as MATLAB, Python, C++, etc., which is easy to grasp and debug the image processing whole process.

The sequence may predefine detailed parameters necessary for the control of a probe, a transmission/reception pulse, a data buffer, an ultrasound device, etc. to be used, and may configure an event sequence operating in an order according to a procedure for each step of an ultrasound image. Each event may be divided into a hardware event of the ultrasound device, such as transmission/reception of ultrasound waves, and a software event of the arithmetic device, such as pulse compression, image restoration, and blood flow signal filtering. The actual processing to be performed in the software event may proceed with the homing of the kernel function of the kernel.

In the kernel, kernel functions defined to process the event sequence generated in the sequence may be configured in parallel. The programming code (script) processed by the kernel is C++-base with a fast computation speed, and among them, Intel Streaming SIMD Extensions (Intel-SSE) or NVIDIA Compute Unified Device Architecture (NVIDIA-CUDA), which are parallel programming languages, are mainly used. Every time it is summoned from the event of the sequence, the input parameter which it is delivered is utilized to perform high-speed operations, output processing results, and repeat it.

The processor 150 according to an embodiment of the present disclosure may transmit an ultrafast ultrasound signal designed according to a transmission mode to a target region and receive the reflected signal, compress a pulse of the reflected signal using a decoding filter according to the transmission mode, obtain an image reconstructing the compressed signal through a dynamic beamforming, remove a fixed tissue signal from the image using a clutter filter, and inversely compensate for an estimated displacement according to motion tracking for a region of interest in the image including a dynamic blood flow signal to generate a pulse-compressed ultrafast Doppler image. At this time, the operations of receiving each of the reflected signals, compressing pulses of the reflected signals, obtaining reconstructed images, removing fixed tissue signals, and generating pulse-compressed ultrafast Doppler images including dynamic blood flow signals may be viewed as an event sequence configured by the above-mentioned sequence.

The processor 150 according to an embodiment of the present disclosure may evaluate the pulse-compressed ultrafast Doppler image using a hemodynamic parameter related to a blood vessel area and a perfusion and a blood vessel skeletal parameter related to a blood vessel density and a blood vessel tortuosity.

Meanwhile, the processor 150 may perform at least some of data analysis, processing, and result information generation for performing the above operations using at least one of a machine learning, a neural network, or a deep learning algorithm as a rule-based or artificial intelligence algorithm. Examples of the neural network may include models such as a Convolutional Neural Network (CNN), a Deep Neural Network (DNN), and a Recurrent Neural Network (RNN).

Figure 3:
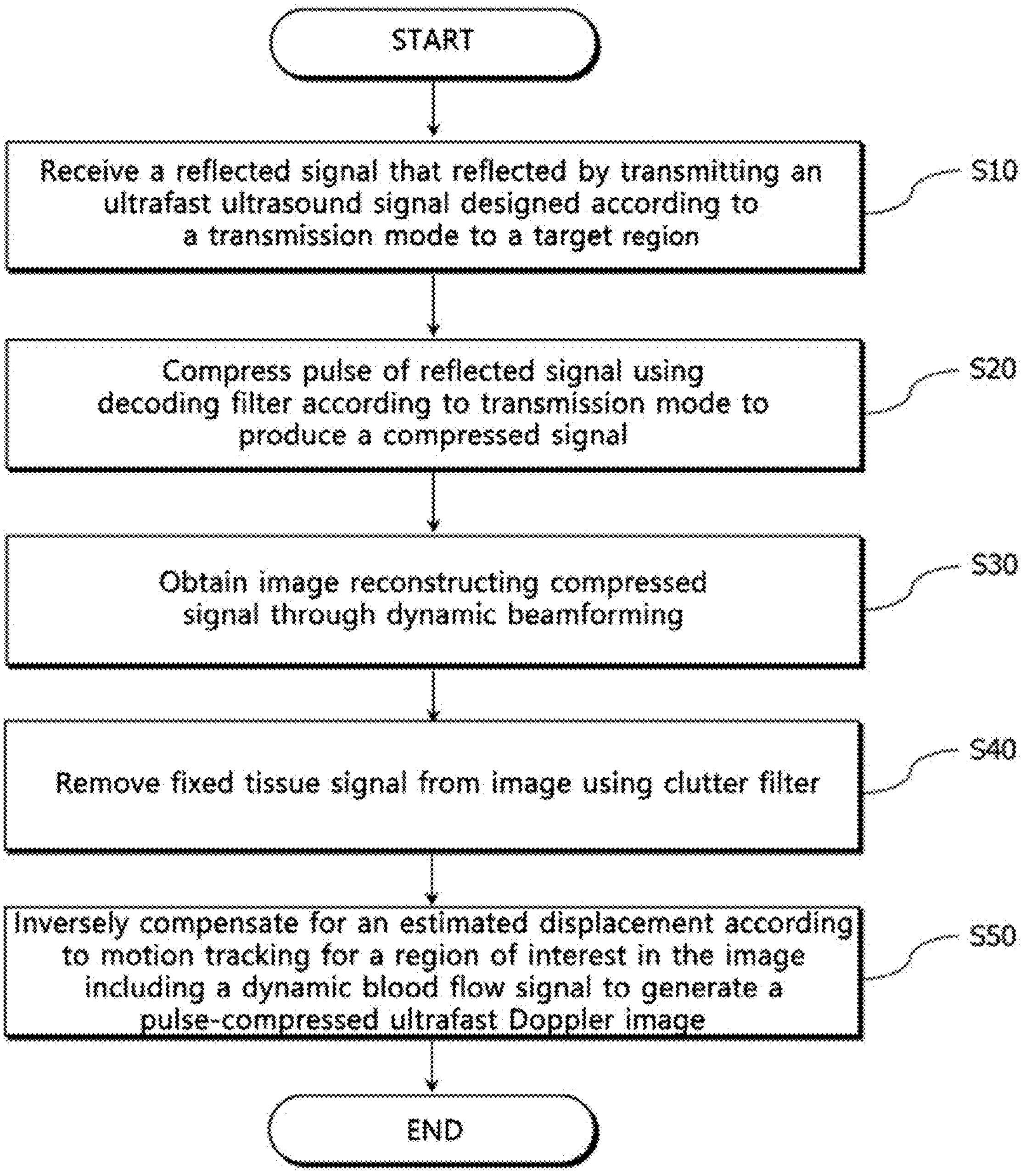
FIG. 3 is a flowchart showing an operation of an information providing device according to an embodiment of the present disclosure.

FIG. 3 is a flowchart showing an operation of an information providing device according to an embodiment of the present disclosure.

The processor 150 according to an embodiment of the present disclosure may be configured to receive a reflected signal that is reflected by transmitting an ultrafast ultrasound signal designed according to a transmission mode to a target region (step S10).

Figure 4:
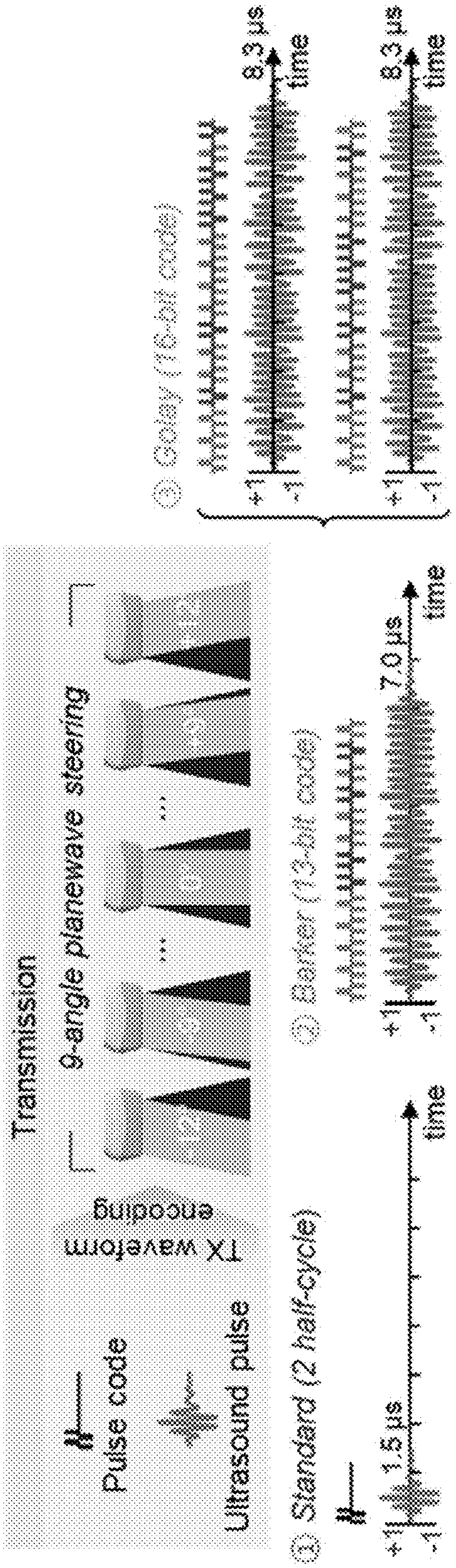
FIG. 4 is a diagram showing an ultrafast ultrasound signal according to an embodiment of the present disclosure.

The ultrafast ultrasound signal may be a binary coded signal according to a transmission mode, and the transmission mode may be a Barker mode or a Golay mode. An example of the ultrafast ultrasound signal according to each mode is shown in FIG. 4.

The ultrafast ultrasound signal coded according to the Barker mode may be designed by synthesizing the Barker code with a basic wavelet. The ultrafast ultrasound signal coded according to the Golay mode may be designed by synthesizing the Golay code with the basic wavelet, and in particular may consist of two signal pairs according to complementary codes.

In this case, the Barker code and the Golay code may be configured in various lengths. (e.g., in the case of Barker, codes having lengths of 2-bit, 3-bit, 4-bit, 5-bit, 7-bit, 11-bit, and 13-bit are known). However, the length of each code may be freely selected and is not limited to any one.

The Barker mode has better temporal resolution than the Golay mode because it acquires more frames in the same amount of time, while the Golay mode has the advantage of better depth-to-noise ratio because it makes pulse compression easier. Therefore, the Barker mode or the Golay mode may be set according to the target region.

The target region is a region in which the deep organs are located, and means the region in which blood flow is to be visualized.

The processor 150 according to an embodiment of the present disclosure may be configured to compress a pulse of the reflected signal using a decoding filter according to the transmission mode (step S20).

The pulse compression is basically 1D synthesis of each column of the reception channel data using a decoding filter. The pulse compression may improve signal-to-noise ratio and image depth without increasing peak acoustic power.

Figure 6:
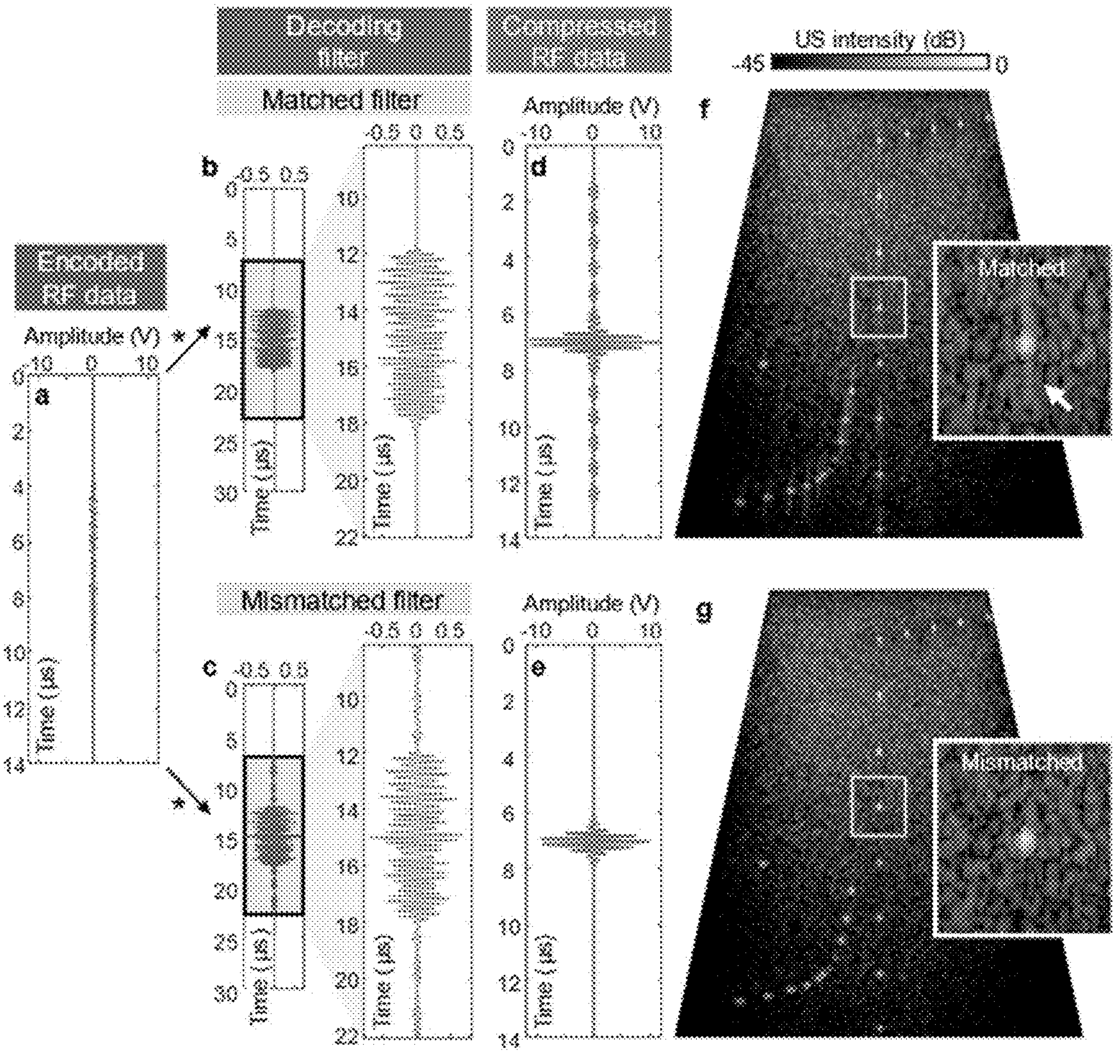
FIG. 6 is a diagram showing a state in which a decoding filter is applied in a Barker mode according to an embodiment of the present disclosure.

The decoding filter may also be designed differently depending on the transmission mode, but in the Barker mode, a mismatched filter based on an integrated side lobe level minimization approach is adopted to suppress sidelobes generated during compression. Accordingly, the processor 150 may compress the pulses of the reflected signal using a decoding filter (also referred to as a mismatched filter) designed to remove the side lobes of the reflected signal in the Barker mode. An example of the mismatched filter adopted in the Barker mode is shown in FIG. 6.

Figure 5:
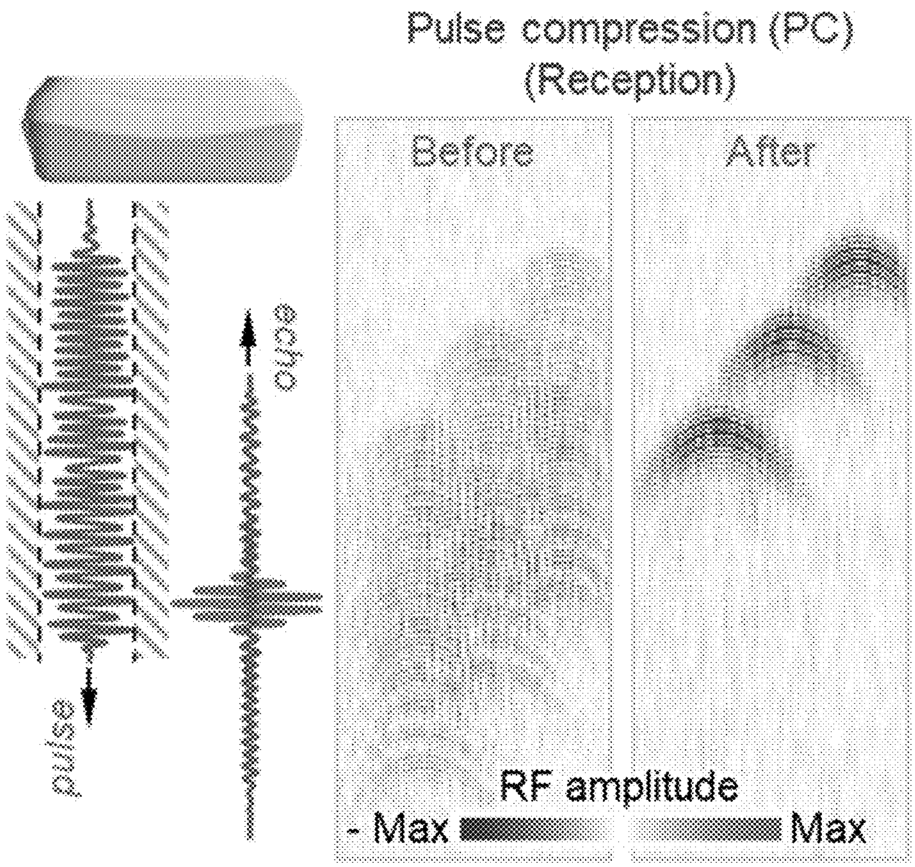
FIG. 5 is a diagram showing a pulse compression according to an embodiment of the present disclosure.

On the other hand, in the Golay mode, the reflected signal is composed of a complementary signal pair, so that the side lobes automatically disappear when two compressed channel data are added. Therefore, the processor 150 may compress the pulses of the reflected signal using the decoding filter (also referred to as a matched filter) designed as an inverse phase of the ultrafast ultrasound signal in the Golay mode. Specifically, in the Golay mode, it may be decoded using a complementary decoding filter pair corresponding to a complementary ultrafast ultrasound signal pair. An example of the decoding filter is shown in FIG. 5.

The processor 150 according to an embodiment of the present disclosure may be configured to obtain an image reconstructing the compressed signal through a dynamic beamforming (step S30).

The dynamic beamforming may be implemented in various ways, for example, may be implemented as time delay-based beamforming.

Figure 7:
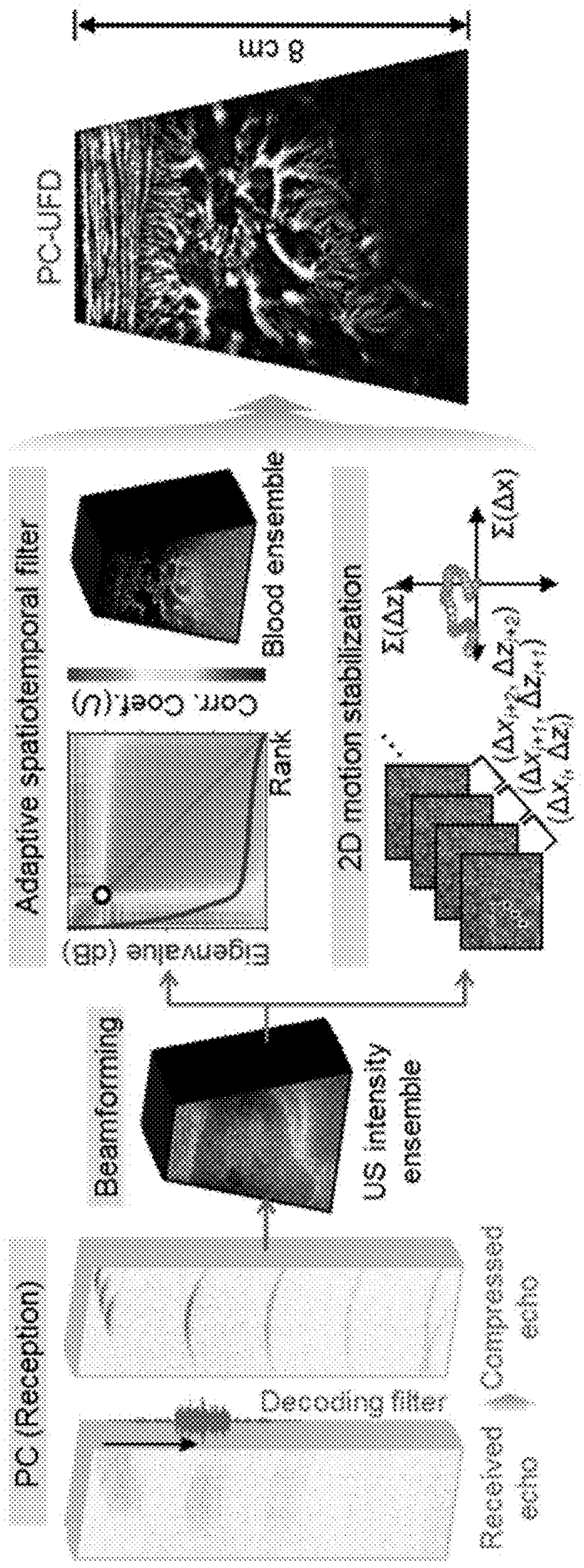
FIG. 7 is a diagram showing a state of obtaining a pulse-compressed ultrafast Doppler image according to an embodiment of the present disclosure.

In the time delay-based beamforming, the decoded channel data may be reconstructed into complex intensity data using a phase rotation-based plane wave synthesis beamformer. This method inversely maps pixel intensities and phase information via a back-projection scheme to explain the time delay calculation of each transducer element for each collection event. When compressed signals are acquired at different ultrasound angles, each may be individually reconstructed and then accumulated to form a single in-phase/quadrature (IQ) intensity data frame. The beamforming is shown in FIG. 7.

The processor 150 according to an embodiment of the present disclosure may be configured to remove a fixed tissue signal from the image using a clutter filter (step S40).

The clutter filter designed to remove the fixed tissue signal from the reconstructed image and leave only a dynamic blood signal may be implemented in various ways. For example, it may be implemented as a singular value decomposition (SVD)-based spatiotemporal clutter filter.

The frames of the image reconstructed through step S30 may be composed of blood flow, tissue, and noise, and when ranking in order of common characteristics of the frames, the tissue that appears stably is ranked at the top, followed by the blood flow and the noise. Therefore, the SVD-based spatiotemporal clutter filter may identify a threshold value of an eigen value based on estimating an inflection point, and distinguish the tissue signal and the blood flow signal within the frame based on the threshold value.

In order to estimate the inflection point, the inflection point may be identified as the farthest point of the eigenvalue curve in this linear plot by displaying the eigenvalues on a logarithmic scale and connecting the first and last ranks.

The processor 150 according to an embodiment of the present disclosure may be configured to inversely compensate for an estimated displacement according to motion tracking for a region of interest in the image including a dynamic blood flow signal to generate a pulse-compressed ultrafast Doppler image (step S50).

The region of interest may be set in a first frame of the image including the dynamic blood flow signal, and the region of interest may be set in the same position in the subsequent frame to estimate the two-dimensional displacement. These displacements are accumulated to calculate the cumulative displacement for the first frame, and each cumulative displacement may be compensated negatively in the corresponding blood signal frame to stabilize the relative motion of the first frame.

The two-dimensional motion is stabilized by inversely compensating for the estimated displacement in sequential frames, and the resulting pulse-compressed ultrafast Doppler image may become more clear.

According to an embodiment of the present disclosure, a pulse-compressed ultrafast Doppler image (PC-UFD) that effectively expands the image depth for the deep organ image and improves the sensitivity of microvascular flow may be demonstrated.

According to an embodiment of the present disclosure, the pulse compression technique may restore long encoded pulses into short pulses and deliver high energy pulses, and as a result, the image depth and the sensitivity of microvascular are greatly improved beyond hardware limitations.

FIG. 4 is a diagram showing an ultrafast ultrasound signal according to an embodiment of the present disclosure.

As described above with respect to step S10 of FIG. 3, FIG. 4 describes a process for acquiring an ultrafast ultrasound signal.

In order to acquire the ultrafast ultrasound signal, a plane wave beam may be transmitted at nine angles (−12°, −9°, −6°, −3°, 0°, +3°, +6°, +9°, +12°), and may be repeated at a maximum pulse repetition frequency (PRF) allowed at a desired image depth (e.g., 6,667 Hz for a depth of 80 mm). A single US ultrasound frame may be configured through the transmission and reception of the plane wave beam adjusted at nine angles.

Meanwhile, each pulse design may be designed using a programmable digital pulse waveform generator essentially supported by the programmable ultrasound device 10. The basic ultrasound signal (standard) is a 5.2 MHz two-half period short ultrasound pulse.

Here, the number or angle of the plane wave beam, the pulse repetition frequency, and the conditions of the basic ultrasound signal are not limited to the examples described above, and the following is the same.

In the Barker mode, the 13-bit Barker code, which has the maximum length and provides the highest sidelobe suppression among the known Barker codes, may be designed. The ultrafast ultrasound signal according to the Barker mode may be generated by combining 13-bit binary Barker codes with basic wavelets (e.g., 1.5% (0.45 μm)). The received channel data may be stored in a reception buffer previously allocated by each transmission mode.

In the Golay mode, the pair of transmission pulses may be designed in a similar manner, but may be generated by synthesizing the same basic wavelet used in the Barker mode with the 16-bit binary Golay code. The Golay decoding requires two complementary sequence transmissions for each pulse search. This doubles the duration of the transmission-reception cycle compared to the non-coded or Barker coding method, and reduces the pulse repetition frequency and frame rate to half, 3,333 Hz and 300 Hz, respectively.

FIG. 5 is a diagram showing a pulse compression according to an embodiment of the present disclosure.

FIG. 5 specifically shows a reflected signal before and after compressing a pulse, as described above with respect to step S20 of FIG. 3. Comparing the received reflected signal before and after pulse compression, it may be seen that the intensity of the signal after pulse compression is stronger, so the image depth and microvascular sensitivity may be greatly improved beyond the hardware limitations.

FIG. 6 is a diagram showing a state in which a decoding filter is applied in a Barker mode according to an embodiment of the present disclosure.

As described above with respect to step S20 in FIG. 3, in the Barker mode, a mismatched filter based on an integrated side lobe level minimization approach is adopted to suppress sidelobes generated during compression.

When the ultrafast ultrasound signal (a) in the encoded Barker mode is decoded through the matched filter (b) and the mismatched filter (c), it may be seen that the compressed signal (d) according to the matched filter (b) generates side lobes around the main signal. On the other hand, it may be seen that the compressed signal (e) according to the mismatched filter (c) that minimizes the side lobe level obtains a signal with the sidelobes suppressed.

In fact, when the images (f and g) are configured using these signals, it may be seen that the image (g) is more clear.

FIG. 7 is a diagram showing a state of obtaining a pulse-compressed ultrafast Doppler image according to an embodiment of the present disclosure.

Referring from the left side of FIG. 7, the reflected signal may be compressed using a decoding filter and processed as an ultrasound intensity frame through a dynamic beamforming. Thereafter, a stabilized blood signal may be filtered using spatiotemporal clutter filtering and two-dimensional motion stabilization and the final microvascular image of the deep organ may be generated through power summation.

The improved pulse-compressed ultrafast Doppler image of FIG. 7 shows complex renal blood vessels, especially interlobular blood vessels with a diameter of less than 400 μm in the renal cortex.

The pulse-compressed ultrafast Doppler image (PC-UFD) according to an embodiment of the present disclosure shows that it is possible to visualize the entire renal blood vessels and differentiate cortical blood vessels with 400 μm or less and quantify hemodynamic and morphological characteristics.

Figure 8:
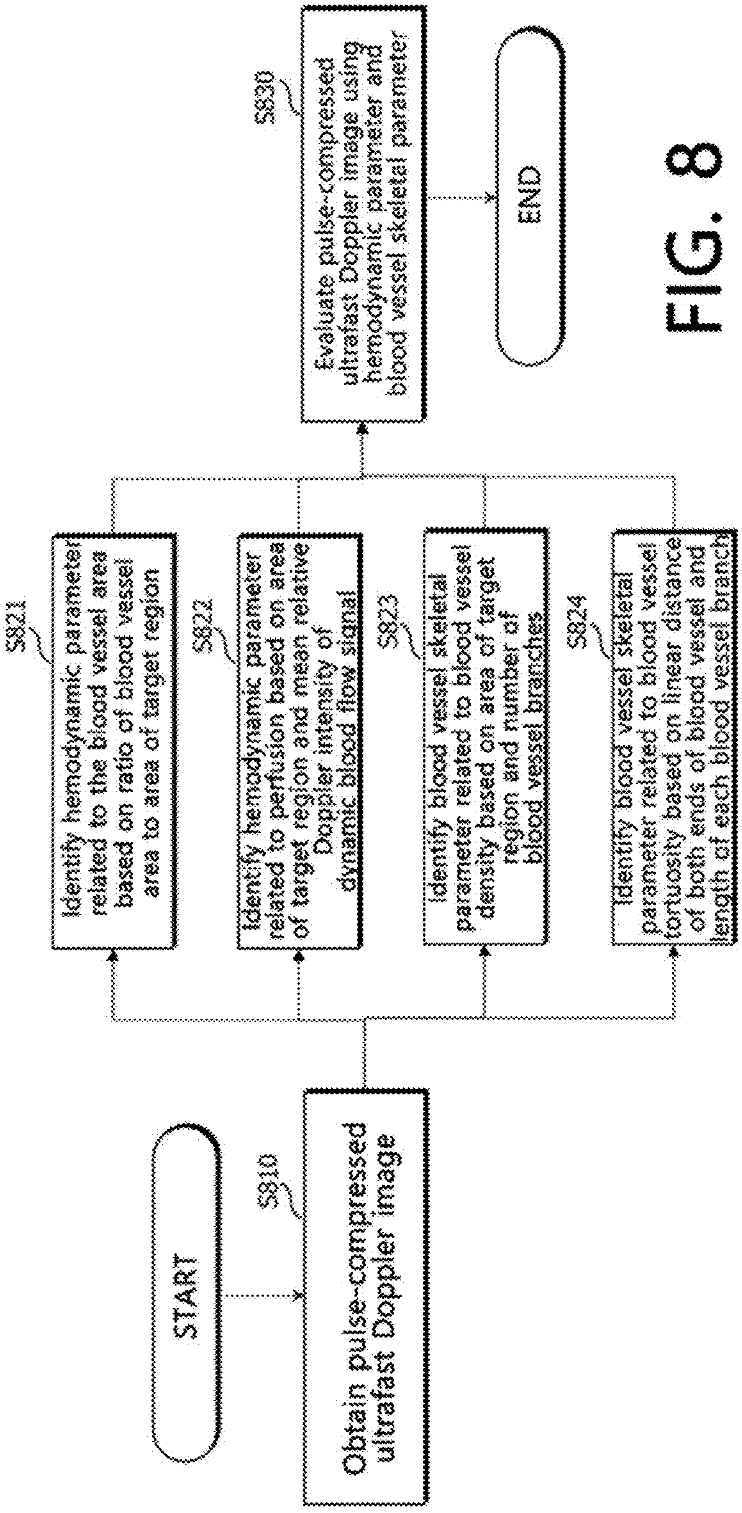
FIG. 8 is a flowchart showing an operation of an information providing device according to an embodiment of the present disclosure.

FIG. 8 is a flowchart showing an operation of an information providing device according to an embodiment of the present disclosure.

This drawing describes a method of evaluating a pulse-compressed ultrafast Doppler image after generating it.

The processor 150 according to an embodiment of the present disclosure may be configured to obtain a pulse-compressed ultrafast Doppler image (step S810). The pulse-compressed ultrafast Doppler image may be an image obtained through the process described with reference to FIG. 3 above.

The processor 150 according to an embodiment of the present disclosure may be configured to identify the hemodynamic parameter related to the blood vessel area based on a ratio of the blood vessel area to an area of the target region (step S821).

The hemodynamic parameter related to the blood vessel area may be calculated by Equation 1 below. Meanwhile, when applied to a three-dimensional image, the hemodynamic parameter related to the blood vessel area is named vessel volume occupancy (VVO), and when applied to a two-dimensional image, the hemodynamic parameter is named cortical vessel occupancy (CVO). Hereinafter, the VVO and CVO are mixed, but this is the difference between 3D (volume) and 2D (cross-sectional area), and the meaning is considered the same.

$$VVO = \frac{v_{vessel}}{v_{target}} \quad \text{[Equation 1]}$$

The $V_{vessel}$ is an area of the blood vessel, and $V_{target}$ is an area of the target region. For example, when the target deep organ is a kidney, the area of the target region may be the volume of the kidney.

Each area may be identified by counting the number of pixels corresponding to the blood vessel or target region in each frame.

The processor 150 according to an embodiment of the present disclosure may be configured to identify a hemodynamic parameter related to perfusion based on the area of the target region and the intensity of the dynamic blood flow signal (step S822).

The hemodynamic parameter related to the perfusion (or fractional moving blood volume, FMBV) may be calculated by Equation 2 below.

$$FMBV = \frac{\sum rPD}{v_{target}} \quad \text{[Equation 2]}$$

The ΣrPD is the Doppler intensity of the dynamic blood flow signal, and $V_{target}$ is the area of the target region.

The FMBV represents the relative perfusion level normalized by the high blood signals of major arteries and veins. Specifically, the ΣrPD may be a value obtained by weighting the signal intensity to the blood vessel area and adding them all together. For example, an intensity of −6 dB or higher may be assigned a value of 100% filled with blood, and an intensity of −18 dB or lower may be assigned a value of 0%.

The processor 150 according to an embodiment of the present disclosure may be configured to identify the blood vessel skeletal parameter related to the blood vessel density based on an area of the target region and the number of blood vessel branches (step S823).

The blood vessel skeletal parameter related to the blood vessel density (or vessel number density, VND) may be calculated by Equation 3 below.

$$VND = \frac{N_b}{V_{target}} \quad \text{[Equation 3]}$$

The $N_b$ is the number of blood vessel branches, and $V_{target}$ is the area of the target region.

The processor 150 according to an embodiment of the present disclosure may be configured to identify the blood vessel skeletal parameter related to the blood vessel tortuosity based on a linear distance of both ends of the blood vessel and a length of each blood vessel branch (S824).

The blood vessel skeletal parameter related to the blood vessel tortuosity (or mean vessel tortuosity, MVT) may be calculated by Equation 4 below.

$$MVT = \frac{\sum\left(\frac{L_b}{d_b}\right)}{N_b} \quad \text{[Equation 4]}$$

The MVT may calculate the ratio of a length of actual blood vessel branch $L_b$ and a linear distance of both ends of the blood vessel $d_b$, and calculate by dividing the sum of the ratios of all branches by the number of branches.

The steps S821 to S824 are parallel, and it does not matter which one is performed first.

The processor 150 according to an embodiment of the present disclosure may be configured to evaluate the pulse-compressed ultrafast Doppler image using a hemodynamic parameter and a blood vessel skeletal parameter (step S830).

Figure 9:
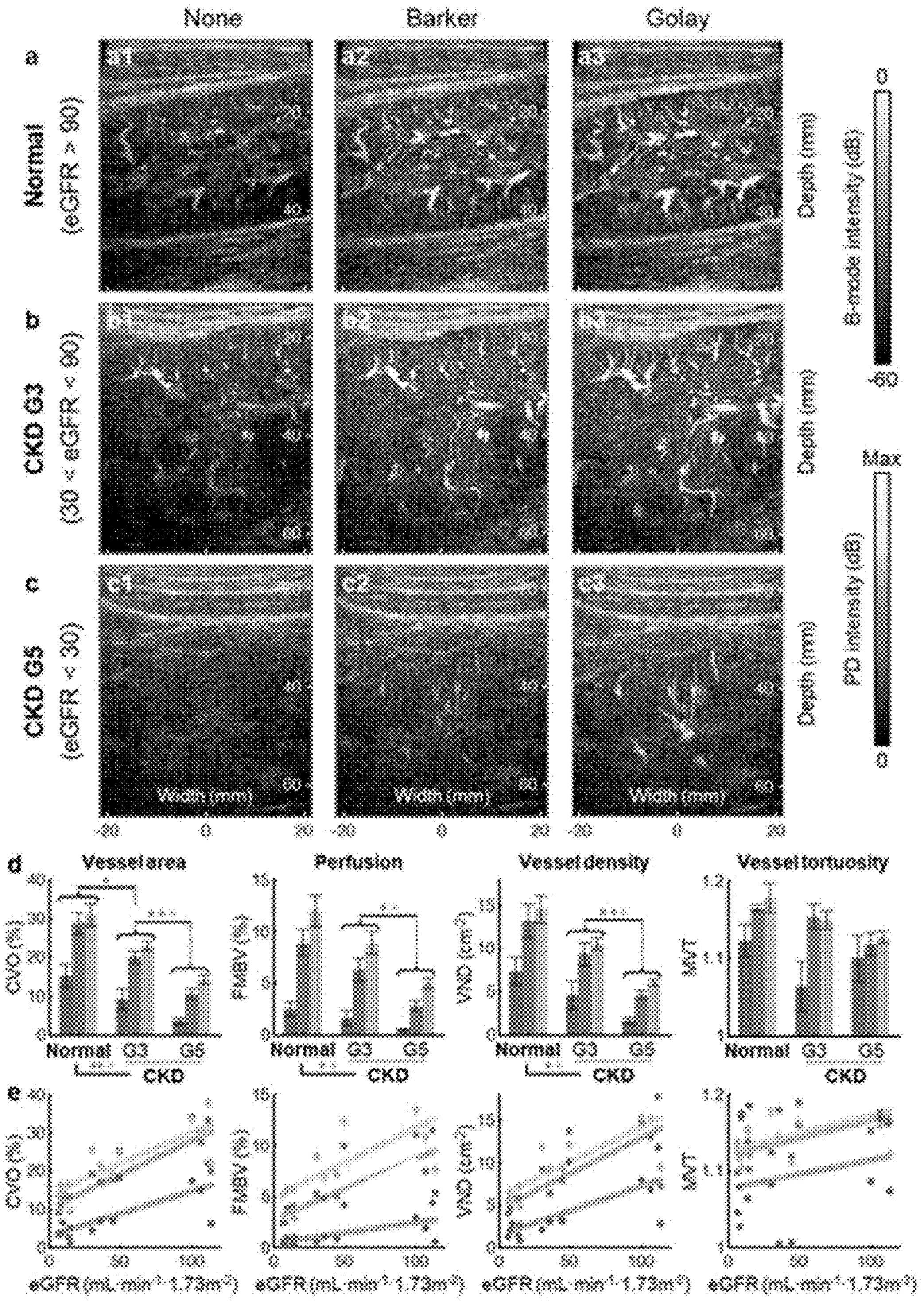
FIG. 9 shows an embodiment of evaluating the pulse-compressed ultrafast Doppler image according to an embodiment of the present disclosure.

FIG. 9 shows an embodiment of evaluating the pulse-compressed ultrafast Doppler image according to an embodiment of the present disclosure.

Acquiring clinical images of kidneys was performed on four healthy volunteers and 11 hospitalized patients diagnosed with chronic kidney disease. Thereafter, the participants were divided into three groups-normal group (n=4), CKD stage 3 group (n=4), and CKD stage 5 group (n=5)-based on estimated glomerular filtration rate (eGFR).

The conventional ultrafast Doppler image (None) showed low contrast overall and faintly visible vascular structure (e.g., a-1, b-1, c-1 in FIG. 9). This makes it difficult to determine whether the blood vessels were not visible because there is no blood vessels or because they are obscured due to depth limitation, and consequently, the sensitivity of the difference between disease groups (CKD G3, CKD G5) and the normal group (Normal) decreased.

In contrast, encoded ultrafast Doppler image (Barker, Golay) with excellent microvascular sensitivity and contrast more clearly emphasized the changes in blood vessels caused by progression of chronic kidney disease (e.g., a-2, a-3, b-2, b-3, c-2, c-3 in FIG. 9).

The Barker-coded ultrafast Doppler image and the Golay-coded ultrafast Doppler image obtained from healthy volunteers were characterized by abundant and clear vascular network across the entire kidneys (e.g., a-2 and a-3 in FIG. 9).

When compared to the densely packed interlobular blood vessel clusters in the cortical area of healthy kidneys, the blood vessels appeared relatively sparse in the CKD stage 3 kidneys, and highlighting a moderate reduction in vascular structure (e.g., b in FIG. 9). Specifically, the arcuate and interlobular vessels became generally thinner, and the branching pattern to finer interlobular vessels became simpler, which may be thought of as a sign of progressive vascular scarcity with the progression of chronic kidney disease.

In all aspects of the area, the number and the intensity of the blood vessels, the severe decrease in kidney circulation in the CKD stage 5 kidneys was noticeable (e.g., c in FIG. 9). There were few blood vessels in the cortical area, leaving very rarely protruding interlobular vessels. In two-dimensional cross-sectional images, coarse shape and weakened connectivity suggest tortuous volume deformation of the vessels.

Quantitative vascular biomarkers were derived from the main features observed in malignant vascular changes, and statistically significant differentiation between participant groups was further verified (e.g., d in FIG. 9). Overall, even within the same participant group, the biomarkers of the encoded ultrafast Doppler images was measured higher than those of the uncoded ultrafast Doppler images. As a result, the progression of chronic kidney disease was more prominent in the encoded ultrafast Doppler image, with ambiguous changes in the biomarkers observed in the uncoded ultrafast Doppler image.

As vascular sensitivity improved, the encoded ultrafast Doppler image detected significantly larger area of the blood vessels, which directly affected the chronic kidney disease index (e.g., d in FIG. 9). The ratio of CVO in the encoded ultrafast Doppler image to that in uncoded ultrafast Doppler image increased progressively with the progression of chronic kidney disease, increasing 2 times in healthy volunteers, 2.3 times in CKD stage 3 patients, and 3.4 times in CKD stage 5 patients. The difference between participant groups in uncoded FMBV was the smallest among quantitative indicators, but at the same time, the amplification of encoded FMBV was the highest (4.2 times, 4.5 times, and 8.3 times in the Normal, CKD3, and CKD5 groups, respectively).

These results directly show the difference in renal perfusion according to severity due to the effective improvement in perfusion sensitivity. The associated decrease in the VND supports the common finding of vascular scarcity with fewer blood vessel segments and sparse branches. The overall decrease in the MVT and the decrease in kidney function in the encoded UFD image suggest a simplification of renal blood vessels in the two-dimensional plane. Unpaired Mann-Whitney U tests between Normal and chronic kidney disease patients, and between Normal and CKD stage 3 patients, demonstrated statistically significant differences in the five quantitative indicators for Barker and Golay-coded UFD. In addition, a strong monotonic proportionality and linear relationship between the measured four quantitative indicators and the glomerular filtration rate (eGFR) were found.

The above contents are shown in Table 1 below.

TABLE 1

| | | | Healthy | CKD | CKD G3 | CKD G6 | P-value Healthy vs. CKD | P-value Healthy vs. CKD G5 | P-value CKD G3 vs. CKD G5 | eGFR Correlation Pearson | eGFR Correlation Spearman |
|---|---|---|---|---|---|---|---|---|---|---|---|
| | | | (n = 4) | (n = 9) | (n = 4) | (n = 5) | | | | | |
| | | eGFR (mL · $min^{-1}$ · $1.73m^{-2}$) | 107.6 | 23.4 | 39.8 | 10.3 | | | | | |
| UFD Parameters | None | Cortical vessel occupancy (%) | 14.5 ± 2.80 | 10.5 ± 2.10 | 3.70 ± 0.70 | 6.70 ± 1.50 | 0.033* | 0.354 | 0.023* | 0.72 | 0.70 |
| | | Fractional moving blood volume (%) | 2.30 ± 0.60 | 1.90 ± 0.60 | 0.50 ± 0.10 | 1.10 ± 0.30 | 0.127 | 0.676 | 0.051 | 0.59 | 0.67 |
| | | Vessel number density (cm-2) | 7.15 ± 1.61 | 5.29 ± 1.21 | 1.76 ± 0.30 | 3.33 ± 0.81 | 0.053 | 0.455 | 0.028* | 0.68 | 0.70 |
| | | Vessel tortuosity | 1.12 ± 0.01 | 1.09 ± 0.03 | 1.11 ± 0.04 | 1.10 ± 0.03 | 0.702 | 0.397 | 0.687 | 0.12 | 0.08 |
| | Barker | Cortical vessel occupancy (%) | 28.9 ± 2.60 | 19.1 ± 1.70 | 10.0 ± 1.30 | 14.1± 1.80 | 0.002** | 0.036* | 0.006** | 0.87 | 0.85 |
| | | Fractional moving blood volume (%) | 9.10 ± 1.20 | 6.00 ± 1.00 | 2.70 ± 0.50 | 4.20 ± 0.80 | 0.007** | 0.138 | 0.028* | 0.81 | 0.84 |
| | | Vessel number density (cm-2) | 13.1 ± 1.84 | 8.67 ± 1.27 | 4.43 ± 0.49 | 6.31 ± 0.94 | 0.007** | 0.139 | 0.021* | 0.80 | 0.77 |
| | | Vessel tortuosity | 1.17 ± 0.01 | 1.16 ± 0.02 | 1.12 ± 0.02 | 1.14 ± 0.02 | 0.226 | 0.621 | 0.316 | 0.50 | 0.47 |
| | Golay | Cortical vessel occupancy (%) | 31.8 ± 2.90 | 24.0 ± 1.40 | 13.6 ± 0.90 | 18.2 ± 1.90 | 0.004** | 0.083 | 0.001** | 0.83 | 0.79 |
| | | Fractional moving blood volume (%) | 12.4 ± 1:50 | 9.30 ± 0.90 | 4.80 ± 0.50 | 6.80 ± 0.90 | 0.011* | 0.183 | 0.005** | 0.79 | 0.79 |
| | | Vessel number density (cm-2) | 14.7 ± 1.62 | 11.2 ± 0.86 | 6.08 ± 0.34 | 8.37 ± 0.96 | 0.008** | 0.154 | 0.001** | 0.81 | 0.79 |
| | | Vessel tortuosity | 1.20 ± 0.03 | 1.15 ± 0.01 | 1.12 ± 0.01 | 1.13 ± 0.01 | 0.015* | 0.203 | 0.012* | 0.71 | 0.66 |

Clinical imaging of 13 primary kidneys in healthy volunteers and hospitalized patients with chronic kidney disease showed pathological vascular scarcity in hemodynamics and morphology along with progression of chronic kidney disease, and could lead to a strong correlation with the decrease in the estimated glomerular filtration rate (eGFR).

Similar decreasing trends were observed in xenografts from three transplant kidney recipients with different grades of CKD, confirming that the technique has the potential to accurately monitor kidney perfusion and identify pathological vascular changes in clinical settings.

Monitoring decreased blood flow using pulse-compressed ultrafast Doppler image may predict renal function impairment due to various complications, and is expected to be widely applied to abdominal organs in addition to the kidney.

Figure 10:
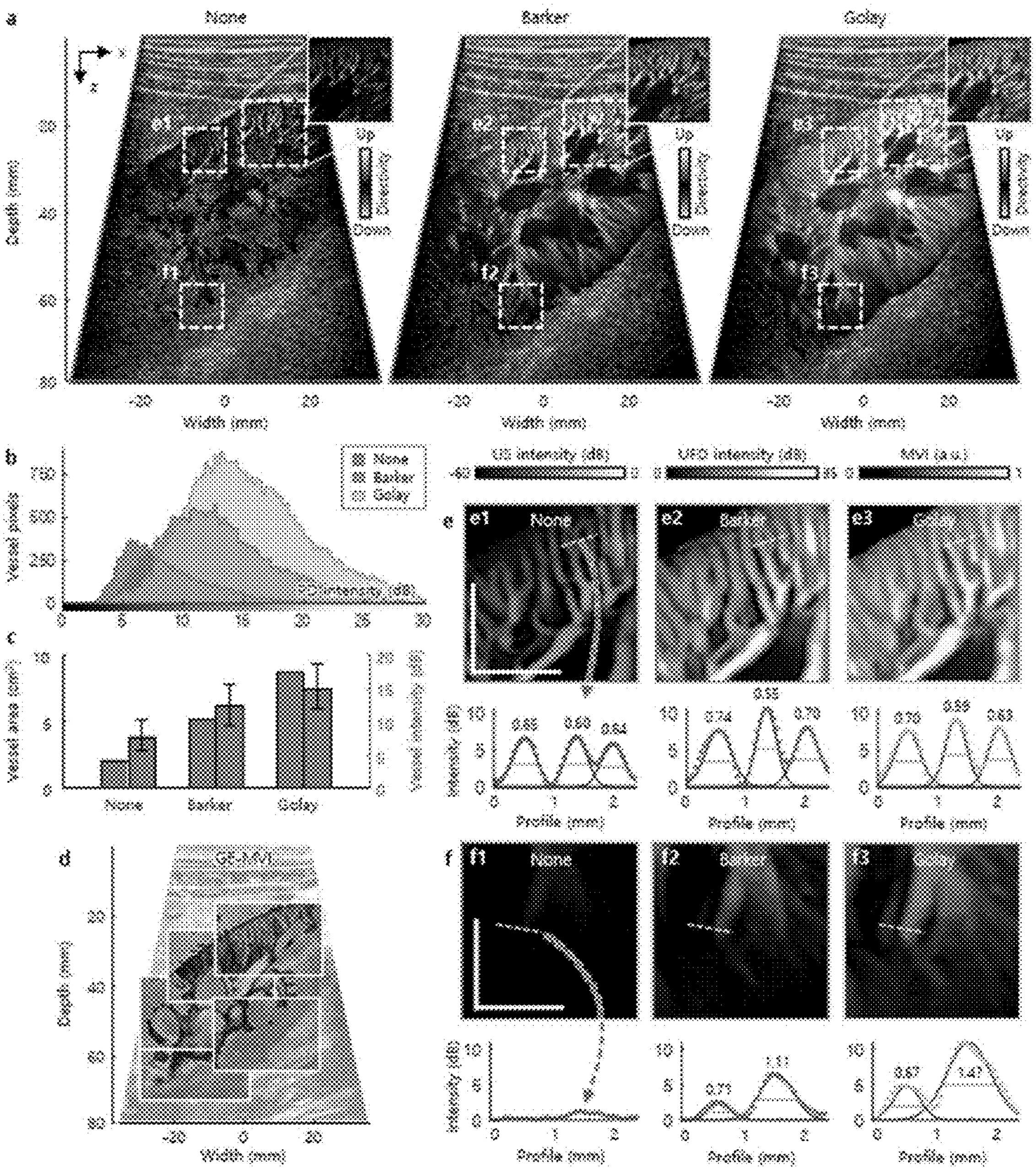
FIG. 10 is a diagram comparing characteristics of a conventional Doppler image and a pulse-compressed ultrafast Doppler image according to an embodiment of the present disclosure.

FIG. 10 is a diagram comparing characteristics of a conventional Doppler image and a pulse-compressed ultrafast Doppler image according to an embodiment of the present disclosure.

Figure 11:
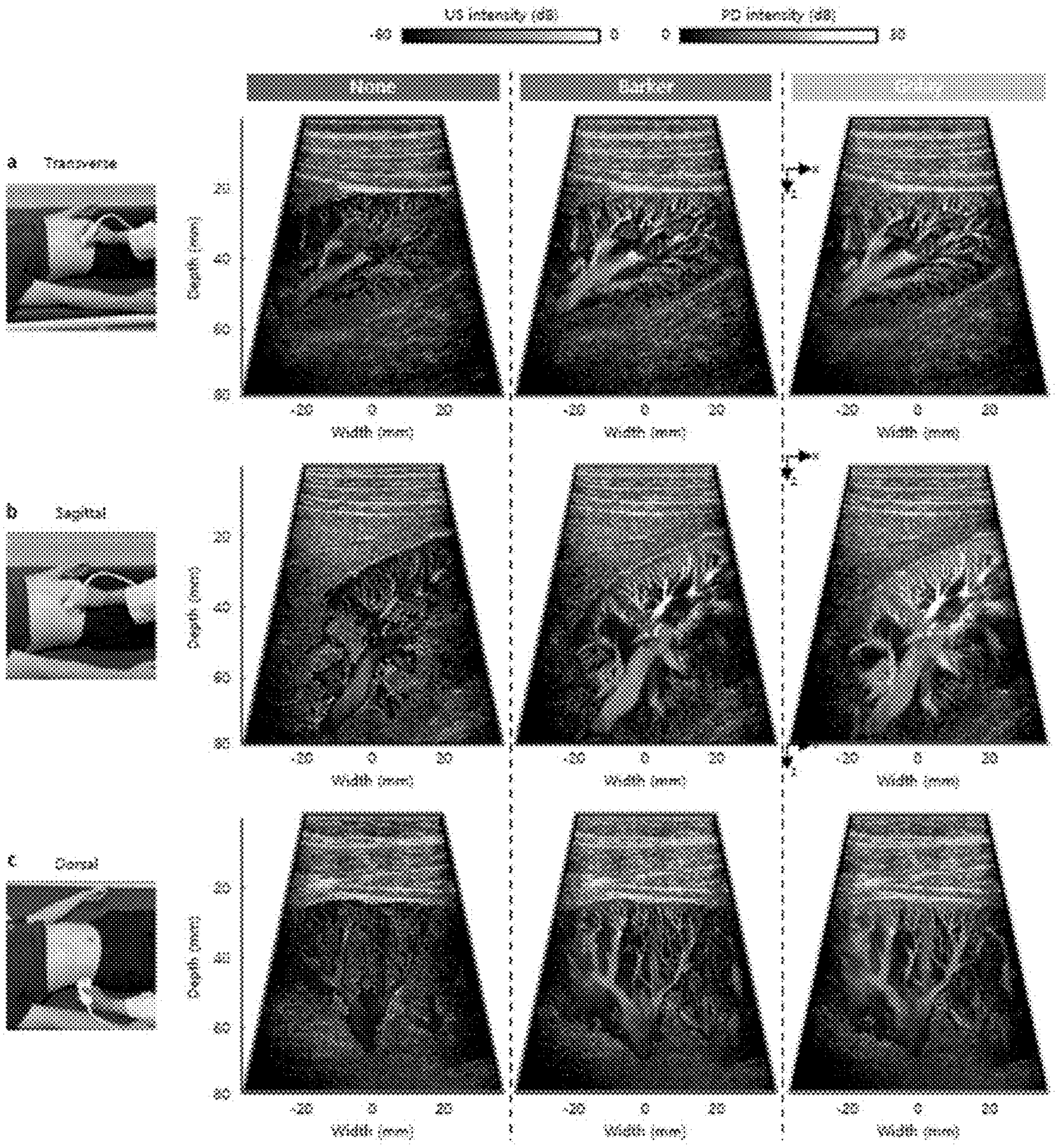
FIG. 11 is a diagram comparing conventional Doppler images at different parts of a deep organ with pulse-compressed ultrafast Doppler images according to an embodiment of the present disclosure.
Figure 12:
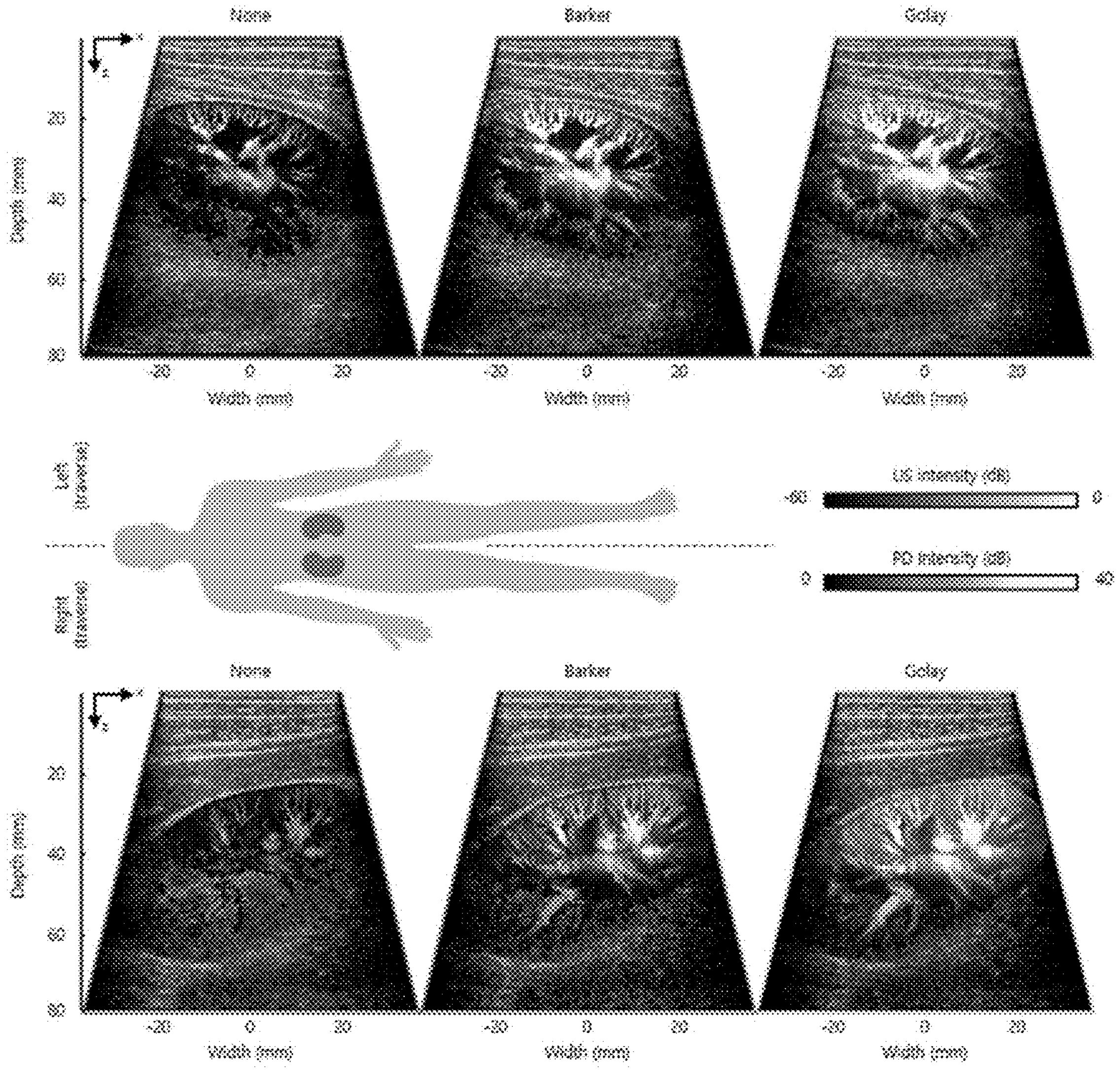
FIG. 12 is a drawing comparing a conventional Doppler image and a pulse-compressed ultrafast Doppler image according to an embodiment of the present disclosure for the left and right portions of a deep organ.

FIG. 10*a* is a diagram showing a renal blood vessel of a right kidney of a healthy volunteer. Sequential acquisitions of three transmission modes (None-mode, Barker mode, and Golay mode) began at the moment when the renal blood vessels appeared 300 frames each at 600 Hz over the entire field of view (FOV). The kidney was imaged in various planes including all cross-sections, sagittal cross-sections, and dorsal longitudinal cross-sections (detailed drawings for this are shown in FIGS. 11 and 12). As representative images, a conventional UFD (None) and two PC-UFD images (Barker, Golay) of the right kidney in the sagittal cross-section are shown in FIG. 10*a*.

The superimposed B-mode images of the kidney clearly show the hierarchical renal blood vessels extending from the renal sinus to the renal capsule. The uncoded ultrafast Doppler image shows significant attenuation effects due to low contrast, with only a few major blood vessels and some interlobular blood vessels near the superficial anterior capsule. In contrast, the ultrafast Doppler images encoded with the Barker and Golay codes completely display vivid blood vessel contrast, revealing a sophisticated and rich vascular network that divides from the renal sinus to the distal renal cortex. Of note, in the image, a rich interlobular blood vessel cluster is seen that extends from 75 mm depth to the posterior capsule as well as near the anterior capsule. The renal blood vessels were masked using a customized blood vessel masking algorithm.

The 30 dB blood vessel pixel distribution of each transmission mode emphasizes a larger power Doppler (PD) intensity and a wider blood vessel area in the pulse-compressed ultrafast ultrasound image than the conventional ultrafast ultrasound image (e.g., b in FIG. 10).

To quantify the enhancement of the blood vessel, the blood vessel area (8.8 $cm^2$) of the Golay-coded ultrafast ultrasound image and the blood vessel area (5.2 $cm^2$) of the Barker-coded ultrasound image were measured to be 4.2 times and 2.5 times larger than the blood vessel area (2.1 $cm^2$) of the conventional ultrasound image (e.g., c in FIG. 10).

In terms of the contrast of the blood vessel, the average PD intensity is the highest in Golay mode (median, 14.9 dB; quartiles Q1-Q3, 11.9-18.6 dB), followed by Barker mode (median, 12.3 dB; 1-3 quartiles Q1-Q3, 9.5-15.8 dB), and is higher than conventional mode (median, 7.6 dB; quartiles Q1-Q3, 5.8-10.4 dB).

This enhancement is generally confirmed on both sides of the kidney (see FIG. 12) and is also confirmed among many volunteers. The depth extension using the pulse-compressed ultrafast Doppler image is much more prominent than the commercial microvascular image (MVI) technology supported by the clinical ultrasound imaging (USI) system (Logiq Fortis, GE Healthcare, USA) (for, d in FIG. 10). In addition, the described interlobular vessels may be further distinguished from peripherally flowing arteries and veins, and from interlobular veins returning to the venous sinus through autocorrelation-based directional estimation.

Focusing on the interlobular blood vessels of the prefrontal cortical area (the upper white dotted line box of a1-a3 in FIG. 10; enlarged view of e1-e3 in FIG. 10) commonly observed in conventional ultrafast Doppler image and pulse-compressed ultrafast Doppler image, cross-sectional blood vessel profiles of adjacent three interlobular blood vessels were extracted to compare spatial resolution. In the transmission mode, subtle differences in vessel diameter were observed (None: 0.65, 0.60 and 0.64 mm; Barker: 0.74, 0.55 and 0.70 mm; Golay: 0.70, 0.59 and 0.63 mm). This demonstrates a preserved spatial resolution.

In contrast, interlobular blood vessels of less than 1 mm in the occipital cortical area are only observable in pulse-compressed ultrafast Doppler images (f1-f3 in FIG. 10). This demonstrates the benefits of pulse-compressed ultrafast Doppler images that may obtain deeper image depths while maintaining spatial resolution.

FIG. 11 is a diagram comparing conventional Doppler images at different parts of a deep organ with pulse-compressed ultrafast Doppler images according to an embodiment of the present disclosure.

The kidney was imaged in various planes including all cross-sections, sagittal cross-sections, and dorsal longitudinal cross-sections.

FIG. 11 is a view of imaging the kidney in various planes including cross sections, sagittal cross-sections, and dorsal longitudinal sections. FIG. 11*a* shows a conventional ultrasound Doppler image (None) and a pulse-compressed ultrasound Doppler image (Barker, Golay) in the Barker and Golay mode in the transverse section of the kidney. FIG. 11*b* similarly shows images viewed from sagittal cross-section of the kidney, and FIG. 11*c* shows the images viewed from the dorsal cross-sections of the kidney.

FIG. 12 is a drawing comparing a conventional Doppler image and a pulse-compressed ultrafast Doppler image according to an embodiment of the present disclosure for the left and right portions of a deep organ.

Although the embodiments of the present disclosure have been described, the spirit of the present disclosure is not limited by the embodiments presented in this specification, and those skilled in the art who understand the spirit of the present disclosure can easily propose other embodiments by adding, altering, deleting, and adding components within the same scope of the spirit, but this is also within the scope of the present disclosure.

The national research and development projects that support this application are as follows.

1. Project Unique Number: 1711137875,
Project Number: KMDF_PR_20200901_0008-02,
Ministry Name: Multi-Ministry,
Project Management (Professional) Agency Name: (Foundation) Inter-Ministry Full-cycle Medical Device Research and Development Project Organization
Research Project Name: Inter-Ministry Full-cycle Medical Device Research and Development Project (R&D) (MSIT, Ministry of Welfare, Ministry of Trade, Industry and Energy),
Research Project Name: (Participation 1) development and commercialization of peripheral microvascular ultrasound photo ultrasound fusion imaging device,
Project Executing Agency Name: Pohang University of Science and Technology,
Research Period: 2020.09.01~2024.12.31.

2. Project Unique Number: 2340004730,
Project Number: 2020R1A6A1A03047902, Ministry Name: Ministry of Education,
Project Management (Specialized) Agency Name: National Research Foundation of Korea,
Research Project Name: Establishment of Academic Research Infrastructure in Science and Engineering,
Research Project Name: Medical Device Innovation Center,
Project Executing Agency Name: Pohang University of Science and Technology,
Research Period: 2024.03.01~2025.02.28.

3. Project Unique Number: 2710015764,
Project Number: 2023R1A2C3004880,
Ministry Name: Ministry of Science and ICT,
Project Management (Specialized) Agency Name: National Research Foundation of Korea,
Research Project Name: Personal Basic Research (MSIT),
Research Project Name: multi-scale multi-mode photo ultrasound imaging using transparent ultrasound transducers,
Project Executing Agency Name: Pohang University of Science and Technology,
Research Period: 2024.03.01~2025.02.28.

4. Project Unique Number: 2710014986,
Project Number: 2021M3C1C3097624,
Ministry Name: Ministry of Science and ICT,
Project Management (Specialized) Agency Name: National Research Foundation of Korea,
Research Project Name: STEAM Research,
Research Project Name: development of cancer-targeted photo acoustic/ultrasound multi-Imaging system,
Project Executing Agency Name: Pohang University of Science and Technology,
Research Period: 2024.01.01~2024.12.31.

5. Project Unique Number: 1711070442,
Project Number: 2011-1-00783-007,
Ministry Name: Ministry of Science and ICT,
Project Management (Specialized) Agency Name: Information and Communication Technology Promotion Center,
Research Project Name: Information and Communication Technology Human Resources Development (R&D),
Research Project Name: Future IT Convergence Research Institute,
Project Executing Agency Name: Pohang University of Science and Technology Industry-Academic Cooperation Group,
Research Period: 2018.01.01~2020.12.31.

6. Project Unique Number: 2710003818,
Project Number: 00335346,
Ministry Name: Ministry of Science and ICT,
Project Management (Specialized) Agency Name: National Research Foundation of Korea,
Research Project Name: Personal Basic Research (MSIT),
Research Project Name: development of real-time ultrasound microvascular imaging system for early detection of diabetic kidney disease,
Project Executing Agency Name: Pohang University of Science and Technology,
Research Period: 2024.05.01~2025.04.30.

7. Project Unique Number: 2710001181,
Project Number: 00211941,
Ministry Name: Ministry of Science and ICT,
Project Management (Specialized) Agency Name: National Research Foundation of Korea,
Research Project Name: Personal Basic Research (MSIT),
Research Project Name: Development of a localized ultrasound therapy and real-time 3D, high-resolution small animal ultrasound brain imaging platform for the treatment of mental disorders,
Project Executing Agency Name: Daegu Gyeongbuk Institute of Science and Technology,
Research Period: 2024.03.01~2025.02.28.

8. Project Unique Number: 2710008944,
Project Number: 2018R1A5A1025511,
Ministry Name: Ministry of Science and ICT,
Project Management (Specialized) Agency Name: National Research Foundation of Korea,
Research Project Name: Group Research Support,
Research Project Name: MAGNETIC INITIATIVE LIFE CARE RESEARCH CENTER,
Project Executing Agency Name: Daegu Gyeongbuk Institute of Science and Technology,
Research Period: 2024.03.01~2025.02.28.

What is claimed is:

1. An information providing device comprising:

a processor configured to:

receive a reflected signal that is reflected by transmitting an ultrafast ultrasound signal designed according to a transmission mode to a target region, compress a pulse of the reflected signal using a decoding filter according to the transmission mode to produce a compressed signal, obtain an image by reconstructing the compressed signal through a dynamic beamforming, remove a fixed tissue signal from the image using a clutter filter, and inversely compensate for an estimated displacement according to motion tracking for a region of interest in the image including a dynamic blood flow signal to generate a pulse-compressed ultrafast Doppler image wherein the processor is configured to:

evaluate the pulse-compressed ultrafast Doppler image using a hemodynamic parameter related to a blood vessel area and a perfusion and a blood vessel skeletal parameter related to a blood vessel density and a blood vessel tortuosity; and identify the blood vessel skeletal parameter related to the blood vessel tortuosity based on a linear distance of both ends of the blood vessel and a length of each of blood vessel branches.

2. The device of claim 1, wherein the processor is configured to:

identify the hemodynamic parameter related to the blood vessel area based on a ratio of the blood vessel area to an area of the target region.

3. The device of claim 1, wherein the processor is configured to:

identify the hemodynamic parameter related to the perfusion based on an area of the target region and a mean relative Doppler intensity of the dynamic blood flow signal.

4. The device of claim 1, wherein the processor is configured to:

identify the blood vessel skeletal parameter related to the blood vessel density based on an area of the target region and the number of blood vessel branches.

5. The device of claim 1, wherein the transmission mode includes a Barker mode or a Golay mode.

6. The device of claim 5, wherein the processor is configured to:

compress the pulse of the reflected signal using the decoding filter designed to remove a side lobe of the reflected signal in the Barker mode.

7. The device of claim 5, wherein the processor is configured to:

compress the pulse of the reflected signal using the decoding filter designed as an inverse phase of the ultrafast ultrasound signal in the Golay mode.

8. The device of claim 1, wherein the processor includes:

a sequence configured to define detailed parameters necessary for generating the pulse-compressed ultrafast Doppler image and configure event sequence operating in stages; and a kernel in which kernel functions defined to process the event sequence generated in the sequence are configured in parallel.

9. An information providing method performed by an information providing device, the method comprising:

receiving a reflected signal that is reflected by transmitting an ultrafast ultrasound signal designed according to a transmission mode to a target region;

compressing a pulse of the reflected signal using a decoding filter according to the transmission mode to produce a compressed signal;

obtaining the image by reconstructing the compressed signal through a dynamic beamforming;

removing a fixed tissue signal from the image using a clutter filter;

inversely compensating for an estimated displacement according to motion tracking for a region of interest in the image including a dynamic blood flow signal to generate a pulse-compressed ultrafast Doppler image; and evaluating the pulse-compressed ultrafast Doppler image using a hemodynamic parameter related to a blood vessel area and a perfusion and a blood vessel skeletal parameter related to a blood vessel density and a blood vessel tortuosity, wherein the evaluating the pulse-compressed ultrafast Doppler image includes:

identifying the blood vessel skeletal parameter related to the blood vessel tortuosity based on a linear distance of both ends of the blood vessel and a length of each of blood vessel branches.

10. The method of claim 9, wherein the evaluating the pulse-compressed ultrafast Doppler image includes:

identifying the hemodynamic parameter related to the blood vessel area based on a ratio of the blood vessel area to an area of the target region.

11. The method of claim 9, wherein the evaluating the pulse-compressed ultrafast Doppler image includes:

identifying the hemodynamic parameter related to the perfusion based on an area of the target region and a mean relative Doppler intensity of the dynamic blood flow signal.

12. The method of claim 9, wherein the evaluating the pulse-compressed ultrafast Doppler image includes:

identifying the blood vessel skeletal parameter related to the blood vessel density based on an area of the target region and the number of blood vessel branches.

13. The method of claim 9, wherein the transmission mode includes a Barker mode or a Golay mode.

14. The method of claim 13, wherein the compressing a pulse of the reflected signal includes:

compressing the pulse of the reflected signal using the decoding filter designed to remove a side lobe of the reflected signal in the Barker mode.

15. The method of claim 13, wherein the compressing a pulse of the reflected signal includes:

compressing the pulse of the reflected signal using the decoding filter designed as an inverse phase of the ultrafast ultrasound signal in the Golay mode.

* * * * *